(12) United States Patent
Nzike

(10) Patent No.: US 9,345,845 B2
(45) Date of Patent: May 24, 2016

(54) NEEDLE HUB AND VALVE FOR NEEDLE HUB

(75) Inventor: Philippe Nzike, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/115,341

(22) PCT Filed: May 4, 2012

(86) PCT No.: PCT/EP2012/058261
§ 371 (c)(1),
(2), (4) Date: Nov. 2, 2013

(87) PCT Pub. No.: WO2012/152700
PCT Pub. Date: Nov. 15, 2012

(65) Prior Publication Data
US 2014/0074044 A1 Mar. 13, 2014

(30) Foreign Application Priority Data

May 6, 2011 (EP) .................................. 11165122

(51) Int. Cl.
*A61M 5/32* (2006.01)
*A61M 39/22* (2006.01)
(Continued)

(52) U.S. Cl.
CPC .............. *A61M 5/3294* (2013.01); *A61M 5/19* (2013.01); *A61M 5/20* (2013.01); *A61M 5/3293* (2013.01);
(Continued)

(58) Field of Classification Search
CPC . A61M 39/22; A61M 39/221; A61M 39/227; A61M 39/24; A61M 2039/2406; A61M 2039/2473; A61M 2039/228; A61M 2005/1787; A61M 2005/2407; A61M 2005/2411; A61M 2005/2474; A61M 2005/2496; A61M 2005/3128; A61M 5/19; A61M 5/3293; A61M 5/3294; A61M 5/34; A61M 5/343; A61M 5/344; A61M 5/345; A61M 5/346–5/348; F16K 17/02; Y10T 137/89676
USPC .................................. 604/99.04, 86–89, 533
See application file for complete search history.

(56) References Cited

U.S. PATENT DOCUMENTS 3,557,778 A * 1/1971 Hughes ................ A61B 5/1438
600/577
3,628,767 A * 12/1971 Lombard ................. 251/129.14
(Continued)

FOREIGN PATENT DOCUMENTS

EP 0710487 A2 5/1996
EP 2283885 A1 2/2011
(Continued)

*Primary Examiner* — Quynh-Nhu H Vu
(74) *Attorney, Agent, or Firm* — McDonnell Boehnen Hulbert & Berghoff LLP

(57) ABSTRACT

The invention is related to an apparatus comprising: a valve body comprising two inlet openings, one outlet opening and a central space connecting the inlet openings and the outlet opening, and a spherical element movably contained inside the central space configured for translatory movement and configured to seal either the first inlet opening or the second inlet opening, wherein each of the inlet openings are configured for fluid communication with a first reservoir and with a second reservoir and wherein the outlet opening is configured for fluid connection with a septum. This apparatus solves the object to make the exchange of used parts including the valve construction less complex. A further object of the invention is to make the exchange easier to handle. The invention is also related to a medical device comprising a dispense interface and an apparatus of the afore-mentioned type.

9 Claims, 14 Drawing Sheets

(51) Int. Cl.
*F16K 17/02* (2006.01)
*A61M 5/19* (2006.01)
*A61M 5/20* (2006.01)
*A61M 5/315* (2006.01)
*A61M 5/34* (2006.01)
*A61M 5/178* (2006.01)
*A61M 5/24* (2006.01)
*A61M 5/31* (2006.01)
*A61M 39/24* (2006.01)

(52) U.S. Cl.
CPC ............... *A61M 39/22* (2013.01); *F16K 17/02* (2013.01); *A61M 5/31546* (2013.01); *A61M 5/34* (2013.01); *A61M 5/345* (2013.01); *A61M 2005/1787* (2013.01); *A61M 2005/2407* (2013.01); *A61M 2005/2474* (2013.01); *A61M 2005/2496* (2013.01); *A61M 2005/3128* (2013.01); *A61M 2039/248* (2013.01); *A61M 2039/2473* (2013.01); *Y10T 137/87676* (2015.04)

(56) References Cited

U.S. PATENT DOCUMENTS

| | | | | |
|---|---|---|---|---|
| 3,957,052 | A | * | 5/1976 | Topham .................... 604/236 |
| 4,044,757 | A | | 8/1977 | McWhorter et al. |
| 4,051,852 | A | * | 10/1977 | Villari .................. A61M 39/02 137/512.3 |
| 4,838,866 | A | * | 6/1989 | Marshall, Sr. ......... A61D 1/025 417/443 |
| 5,139,654 | A | * | 8/1992 | Carpenter ................ G01N 1/12 210/136 |
| 5,378,233 | A | | 1/1995 | Haber et al. |
| 5,626,567 | A | * | 5/1997 | Gmeiner ............... A61M 5/286 604/236 |
| 2007/0272311 | A1 | | 11/2007 | Trocki et al. |
| 2009/0145509 | A1 | * | 6/2009 | Baker ................... A61J 1/2089 141/2 |
| 2011/0208128 | A1 | * | 8/2011 | Wu et al. ....................... 604/247 |

FOREIGN PATENT DOCUMENTS

WO    WO 92/18176 A    10/1992
WO    WO 94/03222 A    2/1994

* cited by examiner

NEEDLE HUB AND VALVE FOR NEEDLE HUB

CROSS REFERENCE TO RELATED APPLICATIONS

The present application is a U.S. National Phase Application pursuant to 35 U.S.C. §371 of International Application No. PCT/EP2012/058261 filed May 4, 2012, which claims priority to European Patent Application No. 11165122.0 filed May 6, 2011. The entire disclosure contents of these applications are herewith incorporated by reference into the present application.

FIELD OF INVENTION

The present patent application relates to medical devices of delivering at least two drug agents from separate reservoirs. Such drug agents may comprise a first and a second medicament. The medical device includes a dose setting mechanism for delivering the drug automatically or manually by the user. Especially the present invention relates to a needle hub and a valve construction for such a needle hub.

BACKGROUND

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

During the use of the dispense interface with two different liquid drug components, wherein either the first or the second liquid drug component is applied to the user, it is necessary to minimize or even eliminate any mixing between both liquid drug components. Therefore the needle hub assembly of the dispense interface includes a valve construction, which is positioned between both fluid pathways built inside needle hub construction being positioned in the dispense interface. Since a multiple use of those parts, which are in contact with the liquid drug components, shall be restricted, those parts have be exchanged regularly.

Thus it is an object of the invention to make the exchange of used parts including the valve construction less complex. A further object of the invention is to make the exchange easier to handle.

These objects may be solved by an apparatus comprising: a valve body comprising two inlet openings, one outlet opening and a central space connecting the inlet openings and the outlet opening, and a spherical element movably contained inside the central space configured for translatory movement and configured to seal either the first inlet opening or the second inlet opening, wherein each of the inlet openings are configured for fluid communication with a first reservoir and with a second reservoir and wherein the outlet opening is configured for fluid connection with a septum.

The valve construction as described before is simple and therefore cheap to produce. The only moving part of the valve construction is the spherical element, which can be inserted into the valve body easily. Thus the exchange of the valve body together with the spherical element is facilitated. At the same time, the pathway for the liquid can be made short, since the volume of the valve body can be restricted to size of minimum movement of the spherical element. Therefore the loss of liquid, especially of a liquid drug component can be reduced.

The valve construction corresponds to a two-way valve. Further the valve construction is controlled by the pressure in the system itself. For example if the first liquid reservoir is set under pressure by activating an injection, the pressure in the liquid pathway into the direction of the first inlet opening of the valve body is raised. This pressure forces the spherical element inside the valve body into the direction of the second inlet opening, until the spherical element is pressed onto the second inlet opening from inside of the valve body. Since the pressure resulting from the first reservoir is strong enough, the second inlet opening is sealed off and hinders the entrance of the second liquid, especially the second liquid drug component into the valve body.

In other words, the spherical element is configured to be pressed against the first inlet opening, while a pressure of a fluid in the other inlet opening is larger than the pressure of a fluid in the first inlet opening. It is further advantageous that the outer diameter of the spherical element is larger than the inner diameter of the inlet opening. Further it is necessary that the diameter of the spherical element and the distance between both inlet openings is adapted, so that, if the spherical element is pressed onto one of the inlet openings, the outlet opening is in fluidic contact with the other inlet opening.

In this way, any mixing of the different liquid components within the valve chamber is prevented and both components can be applied to the user separately with only minimal interference with the other component.

A preferred embodiment is characterized in that the spherical element consists of a core material and a shell like outer material, wherein the core material is harder than the outer material. This shell-like construction of the spherical element is advantageous in that the core material is hard enough to prevent, that the spherical element is drawn into the inlet opening onto which it is pressed. On the other hand the softer outer layer or shell of the spherical element enables that the inlet opening is correctly sealed off, and that any unevenness of the rim of the inlet opening can be compensated.

The above described object can also be solved by a dispense interface configured for fluid communication with a first reservoir and a second reservoir of liquids, especially liquid drug components, comprising a needle hub, wherein the needle hub comprises a valve body comprising two inlet openings, one outlet opening and a central space connecting the inlet openings and the outlet opening, and a spherical element movably contained inside the central space configured for translatory movement and configured to seal either the first inlet opening or the second inlet opening, wherein each of the inlet openings are configured for fluid communication with a first reservoir and with a second reservoir respectively and wherein the outlet opening is configured for fluid connection with a septum.

In a further preferred embodiment the inlet openings are connected via inlet pathways with needles which are configured for fluid communication with the corresponding reservoir. The inlet pathways may be built inside the body of the needle hub, wherein the needle hub may be comprised of at least two parts being detachably connected to each other.

Further the outlet opening can be connected via a holding chamber with a septum, wherein the septum is used to apply a dispense needle for applying the drug component into the skin of a user.

It is thus preferred that the needle hub includes the structure of the valve body and the fluid pathways from the liquid reservoirs to the valve body and from the valve body to the outlet septum. On one hand the valve body, the inlet pathways and the holding chamber are built inside a needle hub of a dispense interface, wherein different parts of the needle hub are matching to each other thereby leaving the spaces building the valve chamber and the fluid pathways. Thus the fluid pathway structure and the valve body may be constructed by two halves of the needle hub to build the structure when fit together.

In another embodiment of the dispense interface the valve body, the inlet pathways and the holding chamber are built as separate elements which are configured to be positioned in a needle hub of a dispense interface. Preferably the separate elements of the fluid pathways are built from thin tubes and needles, wherein the valve chamber is also built by a separate element, to which the fluid pathway elements can be connected by sticking, screwing and/or welding.

Thus the valve and fluid pathway construction described above can be used within a dispense interface of a medical device for applying liquid drug components to a user. It is advantageous that the parts to be changed after the use of the dispense interface during an injection procedure are reduced to a smaller number of parts. Thus waste and costs can be saved.

Further to the embodiments discussed before, the above objects can be solved by a medical device of delivering at least two drug agents from separate reservoirs comprising:

a dispense interface configured for fluid communication with a first reservoir and a second reservoir of liquids, especially liquid drug components, and a needle hub being a part of the dispense interface, wherein the needle hub comprises a valve body comprising two inlet openings, one outlet opening and a central space connecting the inlet openings and the outlet opening, and a spherical element movably contained inside the central space configured for translatory movement and configured to seal either the first inlet opening or the second inlet opening, wherein each of the inlet openings are configured for fluid communication with a first reservoir and with a second reservoir respectively and wherein the outlet opening is configured for fluid connection with a septum.

Thus the advantages of the afore described dispense interface can be achieved with a medical device of delivering at least two drug agents from separate reservoirs.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
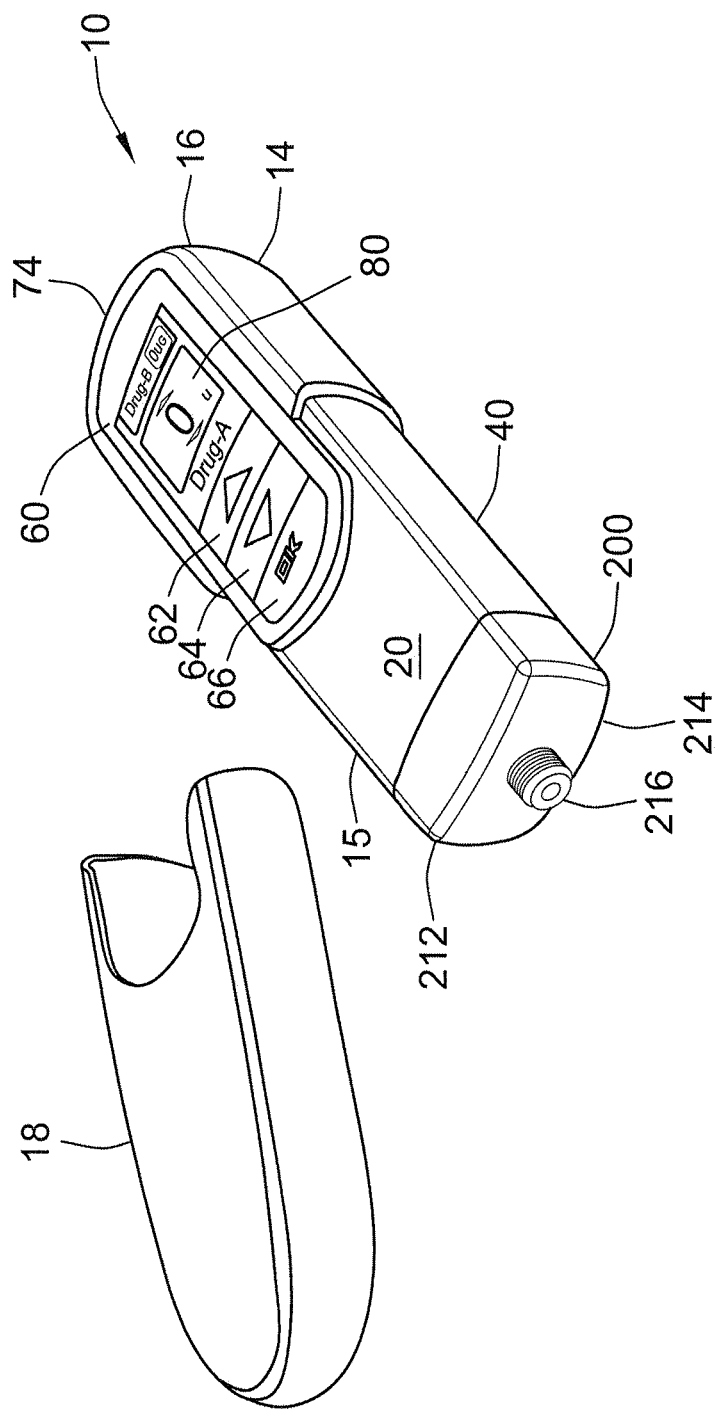
FIG. 1 illustrates a perspective view of a delivery device with an end cap of the device removed.
Figure 2:
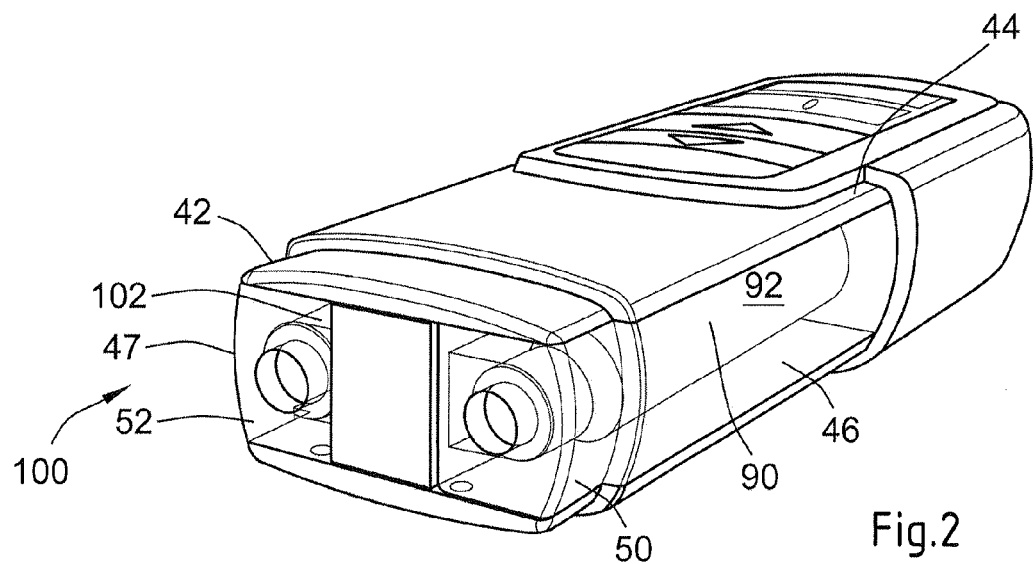
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
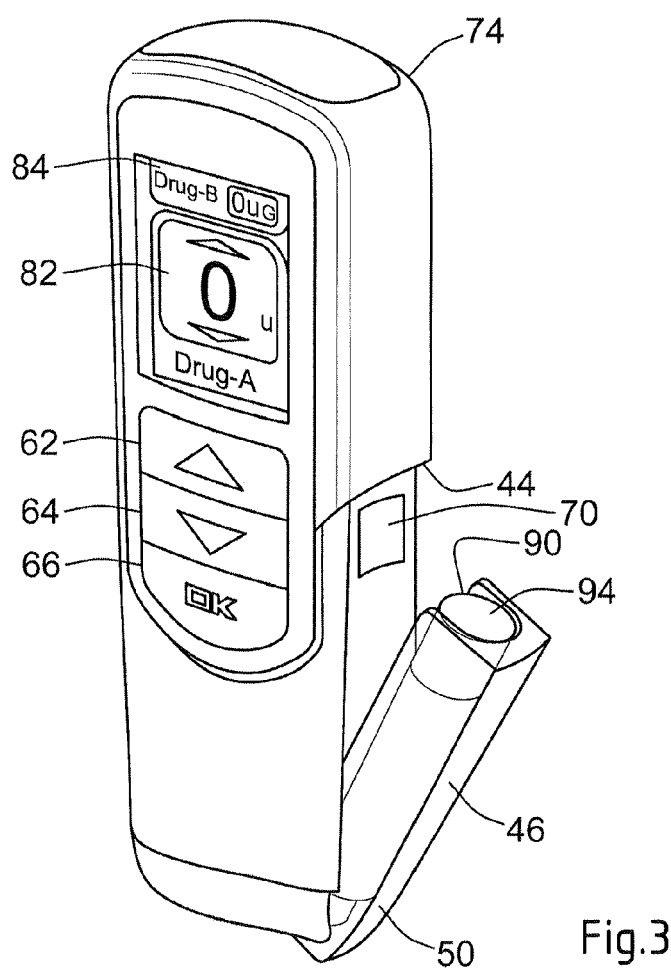
FIG. 3 illustrates a perspective view of the cartridge holder illustrated in FIG. 1 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
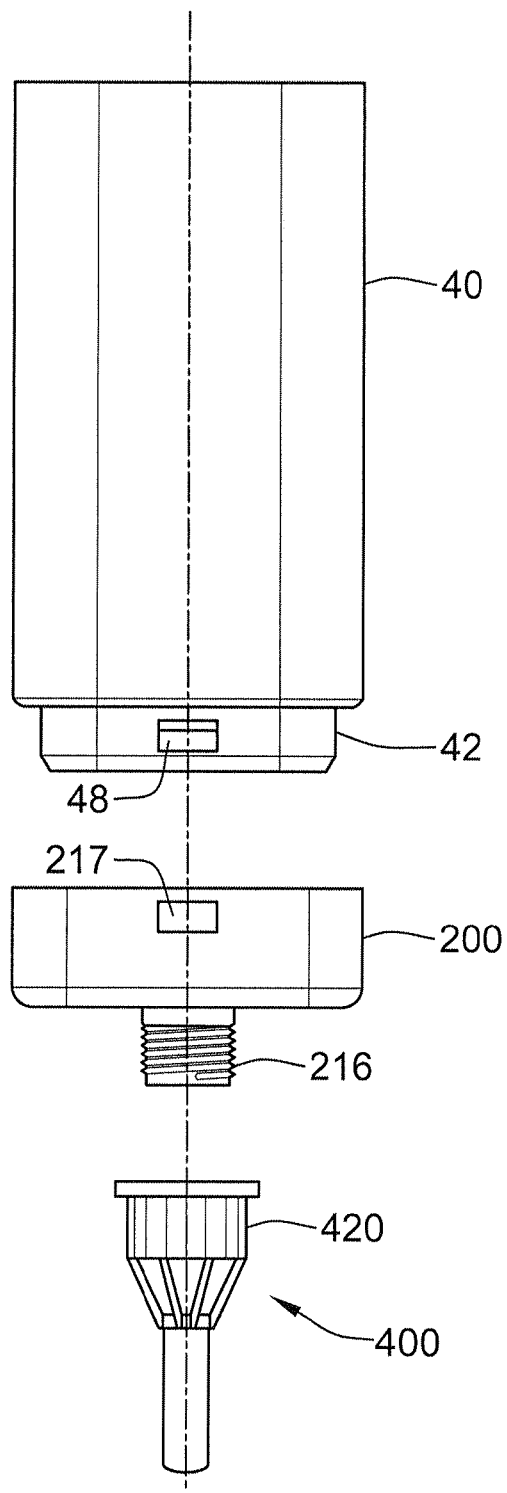
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
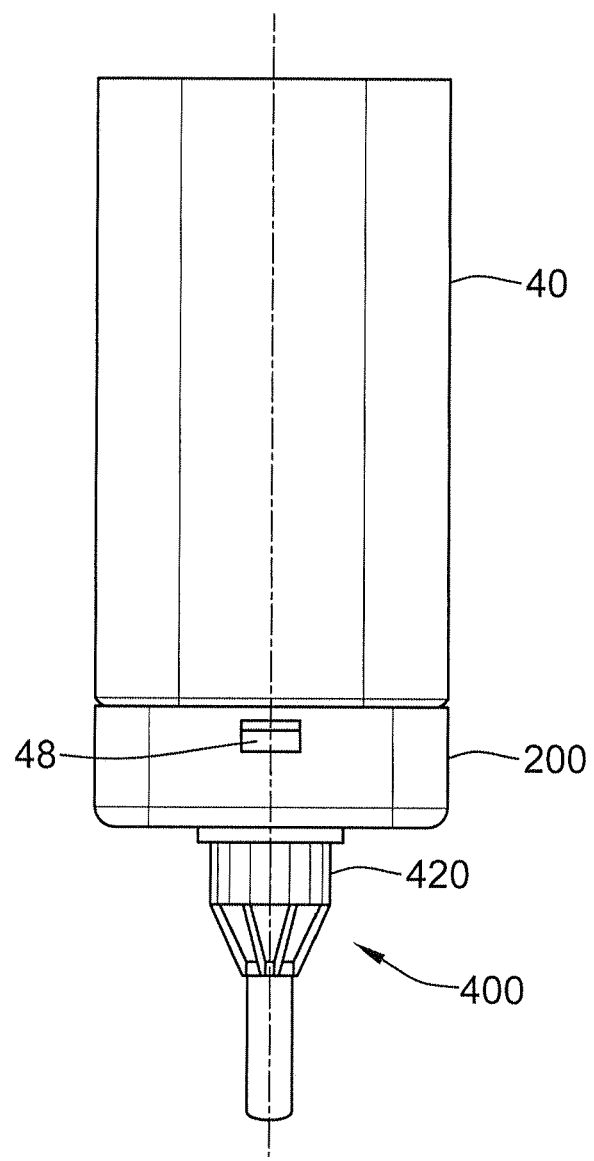
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
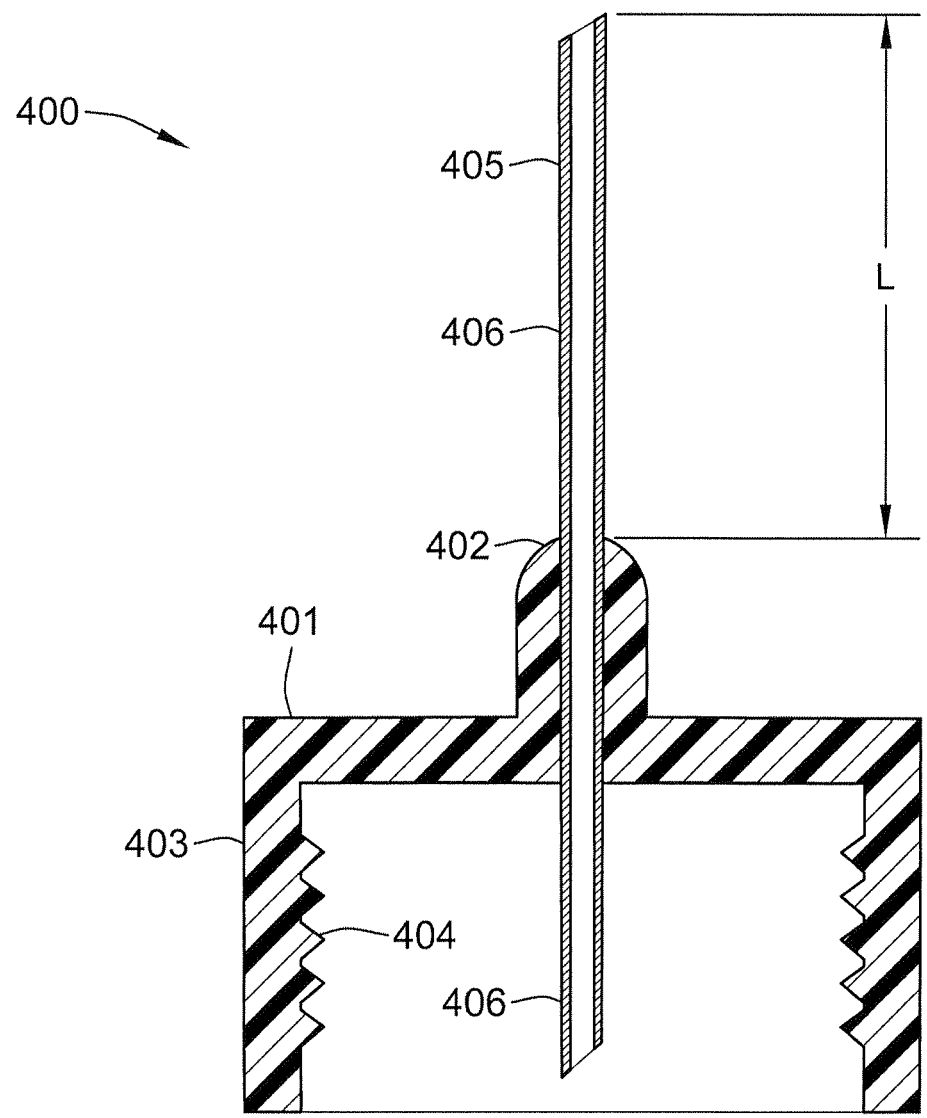
FIG. 6 illustrates one arrangement of the dose dispenser that may be mounted on a distal end of the delivery device.
Figure 7:
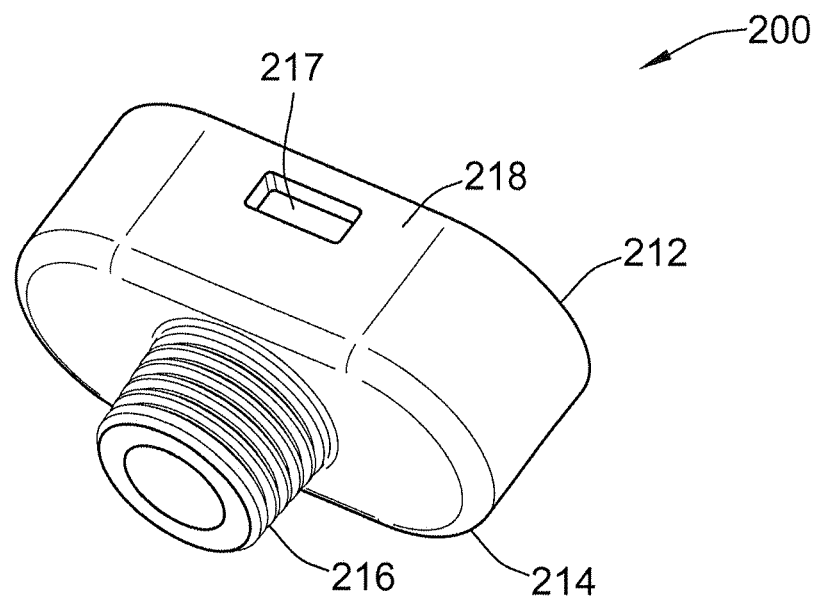
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
 b. an first inner body 220,
 c. a second inner body 230,
 d. a first piercing needle 240,
 e. a second piercing needle 250,
 f. a valve seal 260, and
 g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
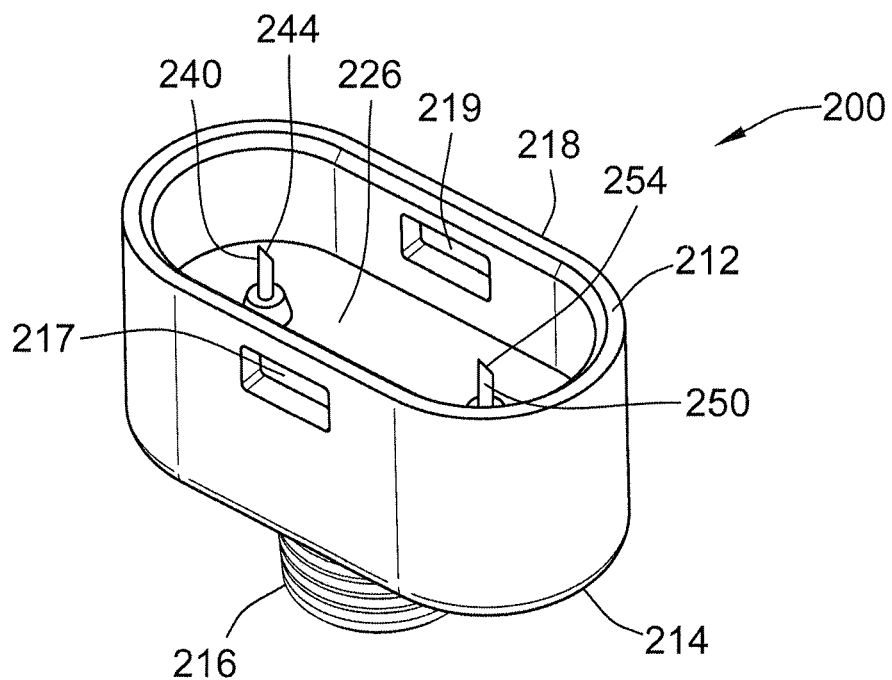
FIG. 8 illustrates another perspective view of the dispense interface illustrated in FIG. 4.
Figure 9:
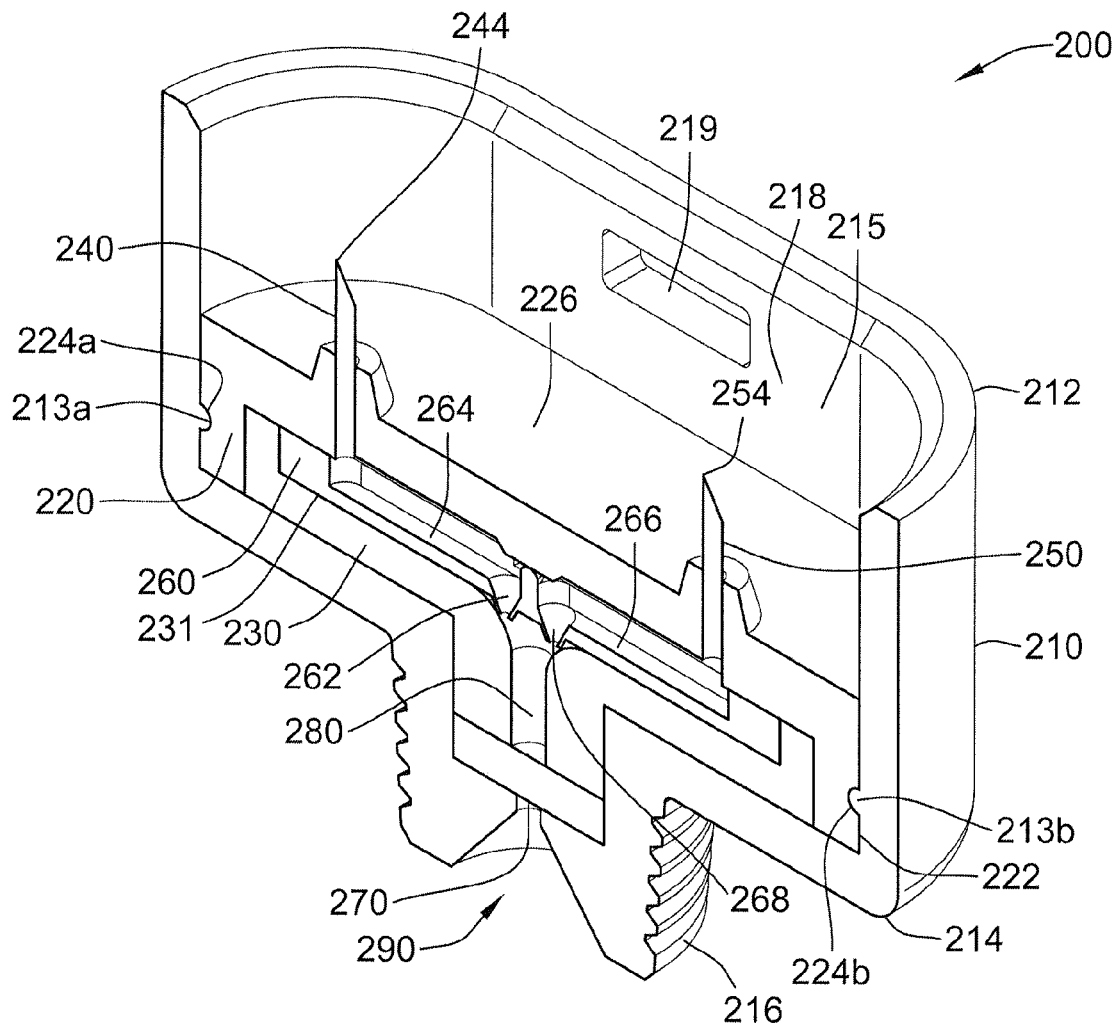
FIG. 9 illustrates a cross-sectional view of the dispense interface illustrated in FIG. 4.
Figure 10:
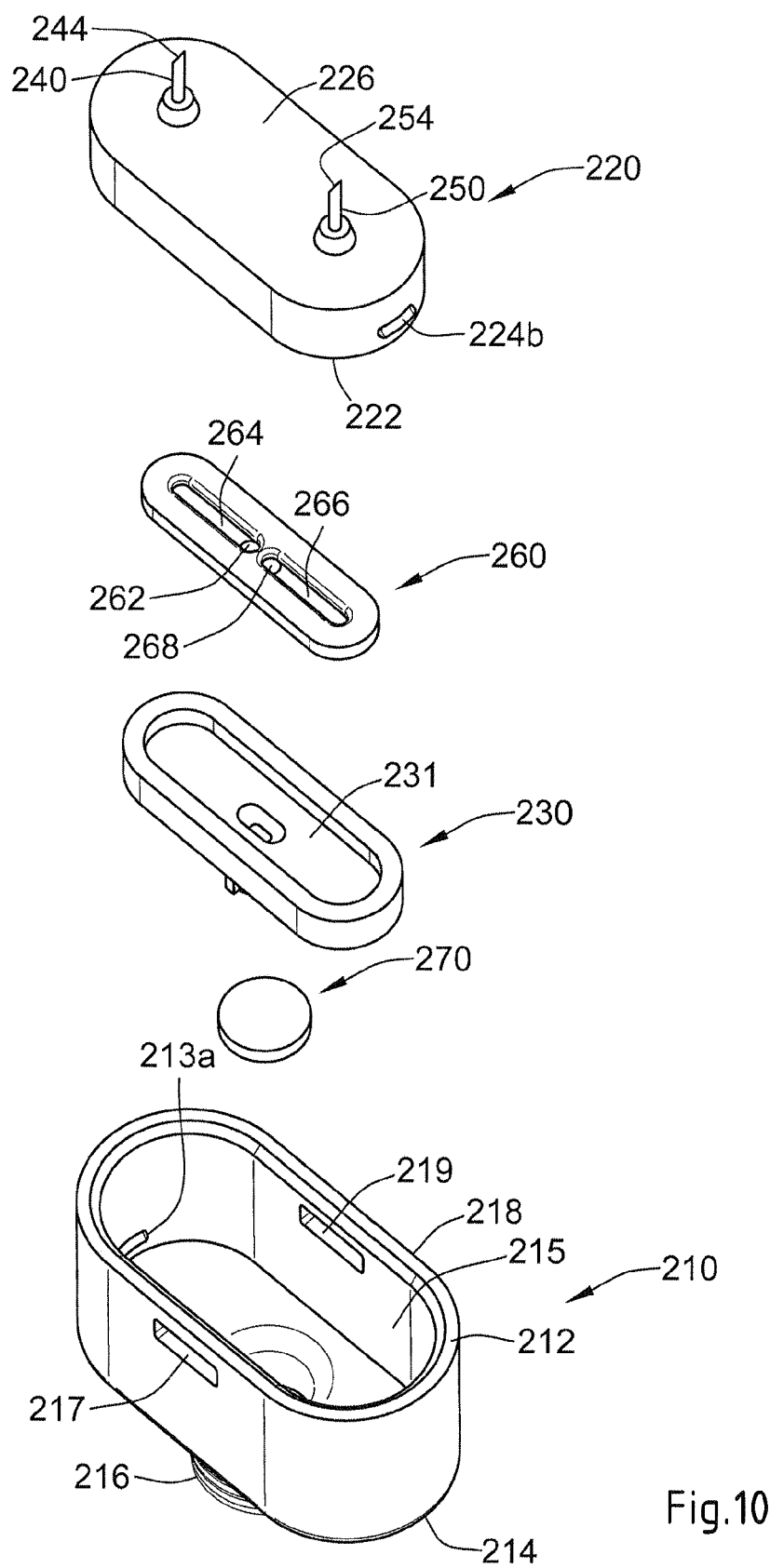
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
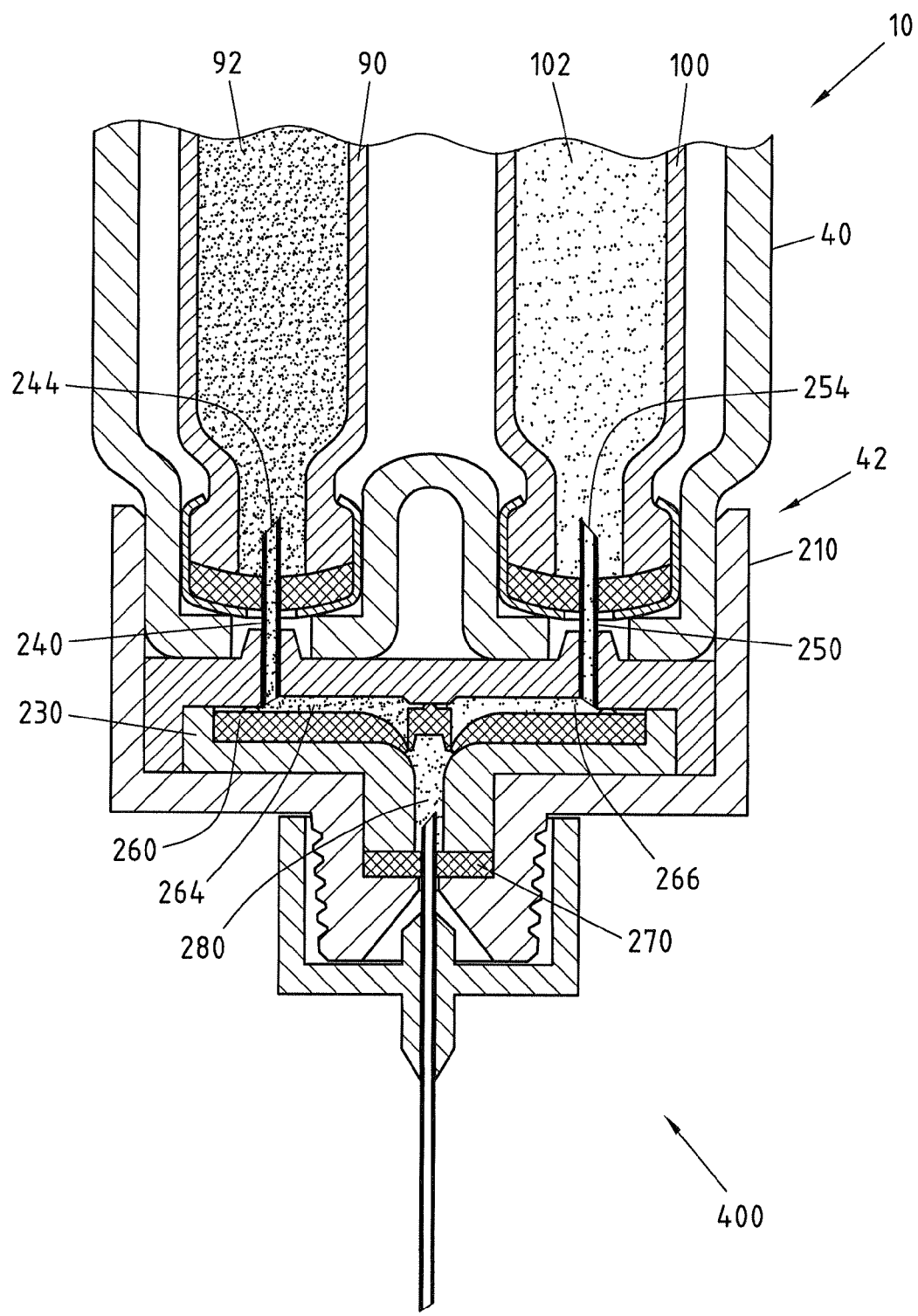
FIG. 11 illustrates a cross-sectional view of the dispense interface and dose dispenser mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

In the following, embodiments of the present invention will be described in detail with reference to FIGS. 12 to 20.

Figure 12:
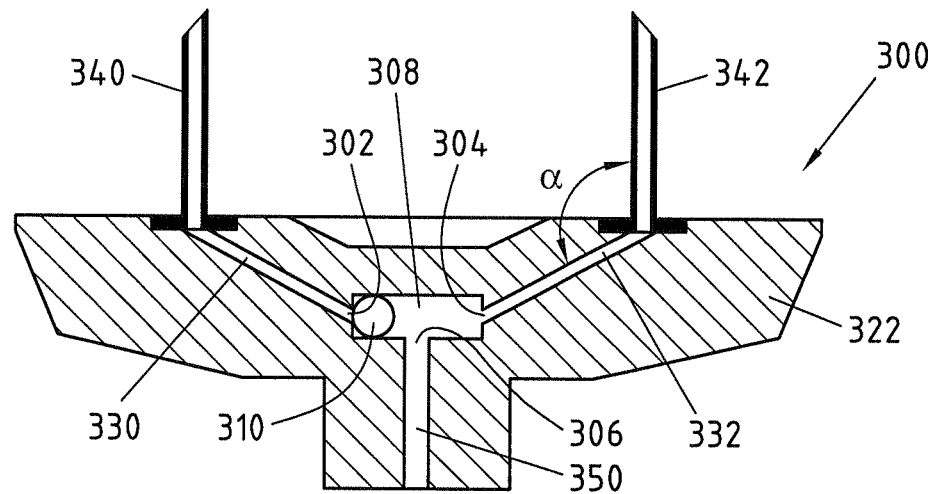
FIG. 12 illustrates a cross-sectional view of an embodiment of the valve body as part of a needle hub including a spherical element in a first position.
Figure 13:
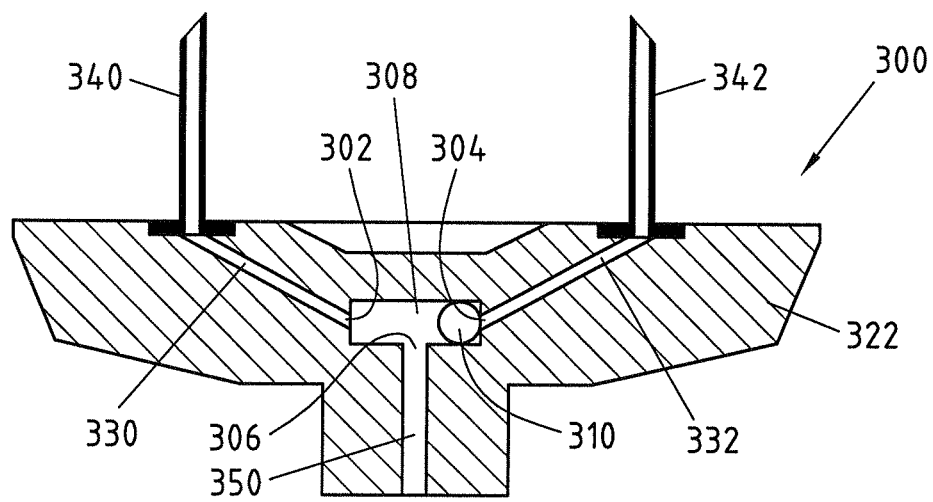
FIG. 13 illustrates a cross-sectional view of the embodiment of the valve body shown in FIG. 12 with a spherical element in a second position.

In FIGS. 12 and 13 cross-sectional views of an embodiment of the valve body 300 are shown, comprising two inlet openings 302 and 304, one outlet opening 306 and a central space 308 connecting the inlet openings 304, 306 and the outlet opening 306. A spherical element or ball 310 is movably contained inside the central space 308 and configured to seal either the first inlet opening 302 or the second inlet opening 304. In this regard FIG. 12 shows the ball 310 in the left position in front of the first inlet opening 302, wherein FIG. 13 shows the ball 310 in the right position in front of the second inlet opening 304.

The inlet openings 302 and 304 are in fluid communication with a first reservoir and with a second reservoir (generally shown for example in FIG. 11 as reservoirs 90 and 100). Further the outlet opening 306 is configured for fluid connection with a septum 270, which has been also discussed with reference to FIG. 11.

The connection between outlet opening 306 and the central space 308 may be configured in such a way that the ball 310 cannot block it. For example, the connection may have a non-circular dimension, for example a rectangle or an oval form, and/or it may be covered by a sieve.

The functionality of the valve is as follows. The spherical element or ball 310 is pressed against the first inlet opening 302 so as to provide a seal which does not allow liquid to pass through, while the fluid in the other inlet opening 304 is under a certain pressure, as is shown in FIG. 12. This pressure is applied, when the liquid drug component in the second reservoir 100 shall be applied and the corresponding drive mechanism is activated. When a pressure is induced in the first reservoir, the situation is as shown in FIG. 13, the ball 310 is pressed against the second inlet opening 304 and gives way for the first liquid drug component to flow from inlet opening 302 through the chamber 308 to the outlet opening 306. As can be seen from FIGS. 12 and 13, the outer diameter of the spherical element 310 is larger than the inner diameter of the inlet openings 302 and 304.

Figure 14:
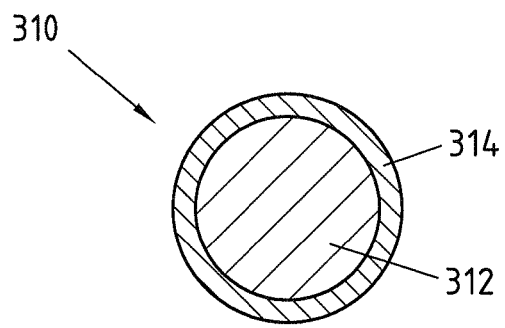
FIG. 14 illustrates a cross-sectional view of the embodiment of the spherical element showing two different materials.

FIG. 14 illustrates that the spherical element may consist of a core material 312 and an outer material 314, wherein the core material 312 is harder than the outer material 314. The different hardnesses of both materials 312 and 314 is advantageous, since the harder inner core of the ball 310 prohibits that the ball is pressed inside the inlet opening 302 or 304, and the softer out material ensures that any unevenness of the rim of the inlet openings 302 and 304 is well sealed even if the pressure in the chamber 308 is low.

Figure 15:
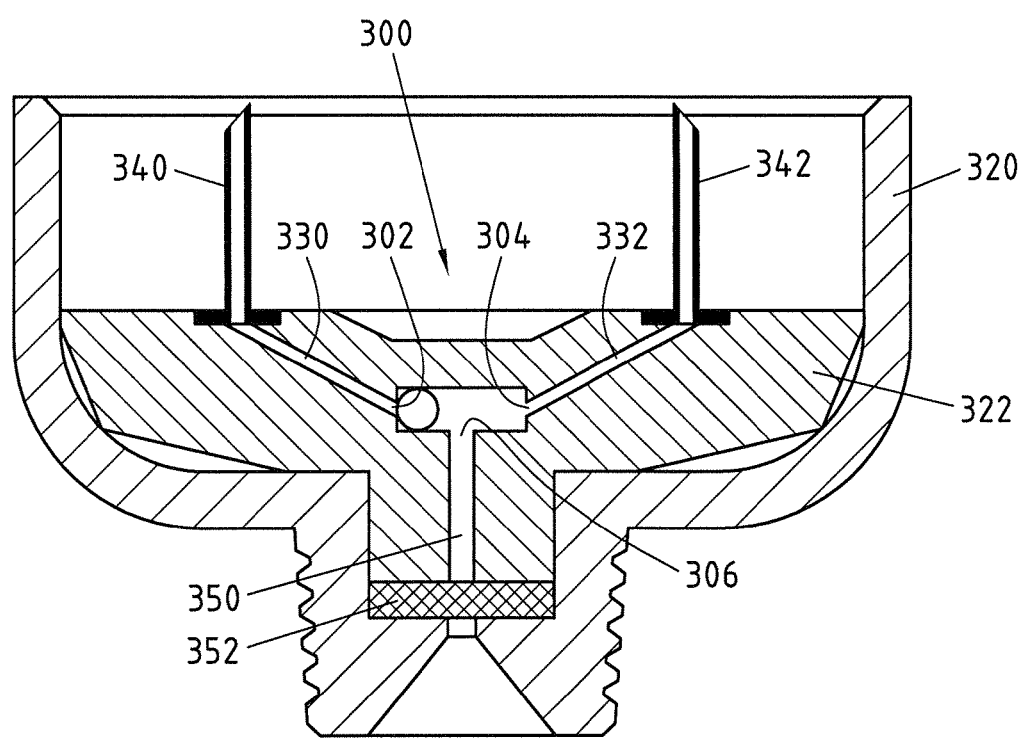
FIG. 15 illustrates a cross-sectional view of an embodiment of the needle hub including the valve body and the spherical element in a first position as shown in FIG. 12, mounted in a dispense interface.

As shown in FIG. 15, a dispense interface 320 is configured for fluid communication with a first reservoir and a second reservoir of liquids, especially liquid drug components. The dispense interface includes a needle hub 322 which is integrated into the dispense interface 320. The needle hub 322 includes the valve construction as described with reference to FIGS. 12 and 13 and is therefore suitable to be applied to a delivery device 100 with cartridge holder 40 as shown for example in FIGS. 1 to 5.

The inlet openings 302 and 304 are connected via inlet pathways 330 and 332 with needles 340 and 342 which are configured for fluid communication with the corresponding reservoir. Further the outlet opening 306 is connected via a holding chamber 350 with a septum 352.

As can be seen from FIG. 15 the valve body 300, the inlet pathways 330 and 332 and the holding chamber 350 are built inside a needle hub 322 of a dispense interface 320. Thus there are provided grooves and indentations, so that when all parts of the needle hub 322 are assembled, the corresponding hollow structure is built.

Figure 16:
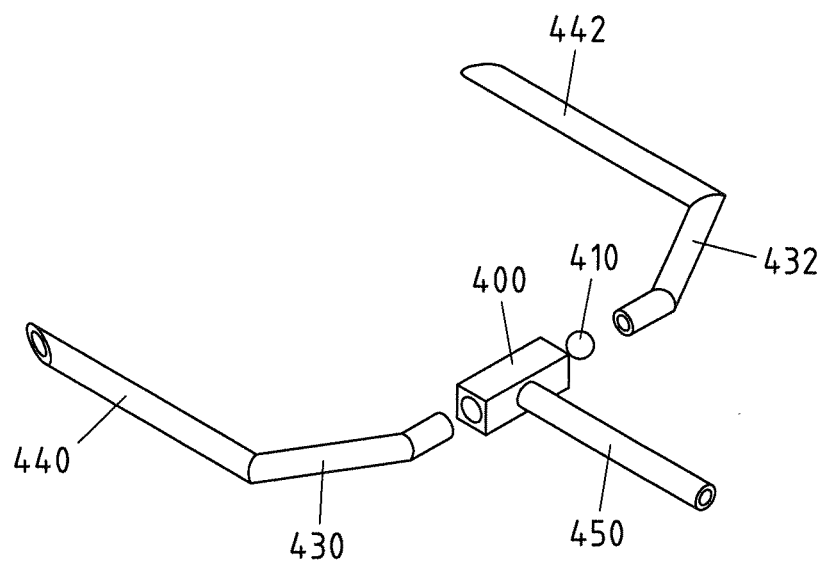
FIG. 16 illustrates a perspective view of an embodiment of the valve body, including a spherical element, and of fluid pathways and the holding chamber built as separate elements.

FIG. 16 illustrates a perspective view of a further embodiment of the valve body 400, including a spherical element 410, and of fluid pathways 430 and 432 and the holding chamber 450 built as separate elements.

Figure 17:
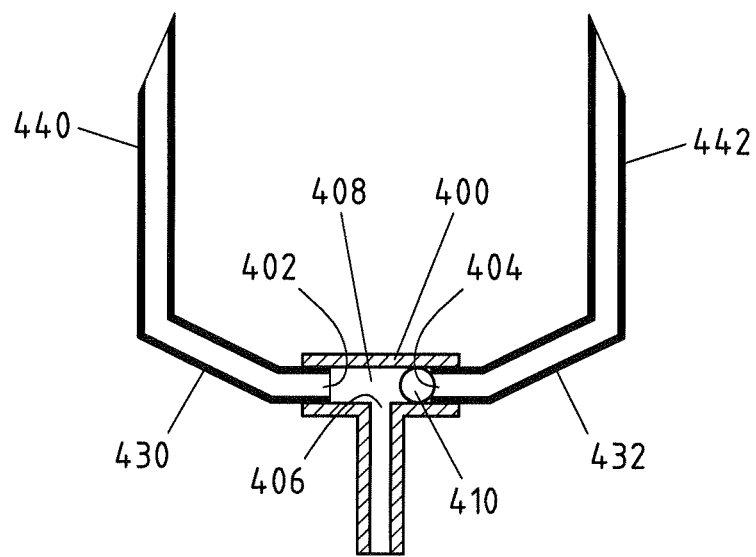
FIG. 17 illustrates a cross-sectional view of the embodiment shown in FIG. 16.

As also can be seen from the cross-sectional view of FIG. 17, the valve body 400 includes inlet openings 402 and 404 as well as an outlet opening 406 limiting a central space 408. The inlet pathways 430 and 432 and the holding chamber 450 are built as separate tubes, which can be connected to the valve chamber 400 simply by a frictional fit, by screwing, by gluing or by welding. The tubes 430 and 432 are further integrally connected with needles 440 and 442. Before attaching all tubes 430, 432 and 450 to the valve chamber 400, the ball 410 is introduced into the valve chamber 400.

The functionality of this valve and pathway assembly is the same as described above with reference to FIGS. 12 and 13. The spherical element or ball 410 is able to seal both inlet openings 402 and 404 respectively, if the liquid in the corresponding other inlet opening 404 and 402 respectively is set under pressure.

Figure 18:
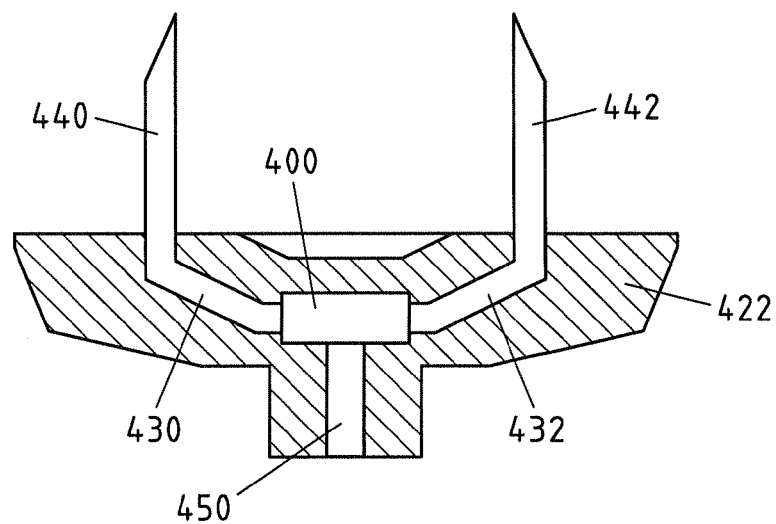
FIG. 18 illustrates a cross-sectional view of an embodiment of the needle hub, wherein the valve construction of FIGS. 16 and 17 is mounted onto the needle hub.

FIG. 18 illustrates a cross-sectional view of the needle hub 422. The needle hub 422 is constructed on one hand to fit into the interior of a dispense interface 420, shown in FIG. 20, and on the other hand to carry the valve and fluid pathway construction as shown in FIGS. 16 and 17. The needle hub 422 is therefore constructed of two halves 422a and 422b, which can be detachably connected to each other.

Figure 19:
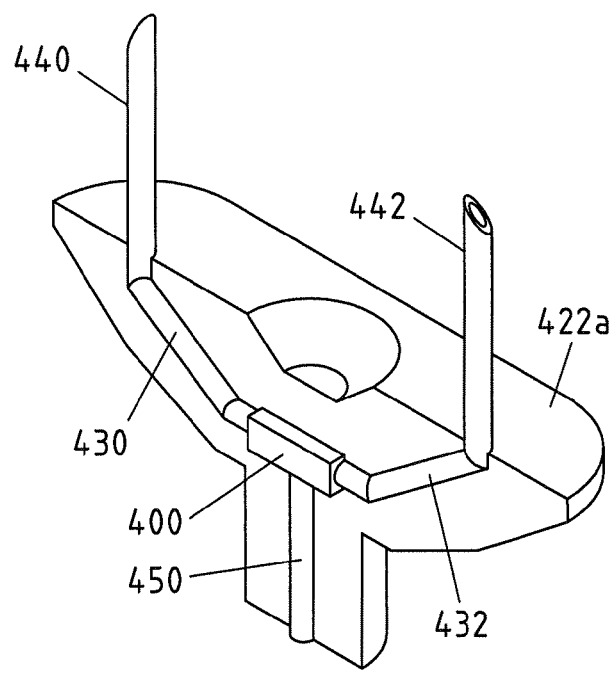
FIG. 19 illustrates a perspective view of a half of the needle hub assembly of FIG. 18

FIG. 19 illustrates a perspective view of one half 422a of the needle hub assembly 422 of FIG. 18. Since all parts of the valve and pathway assembly are made as separate parts, they can be easily exchanged. That means, that if the valve and fluid pathway assembly has been used and has to be exchanged, the needle hub 422 is taken apart and the used valve and fluid pathway construction can be exchanged to a new one. Thus the amount of waste for every change of used materials is reduced to a minimum.

Figure 20:
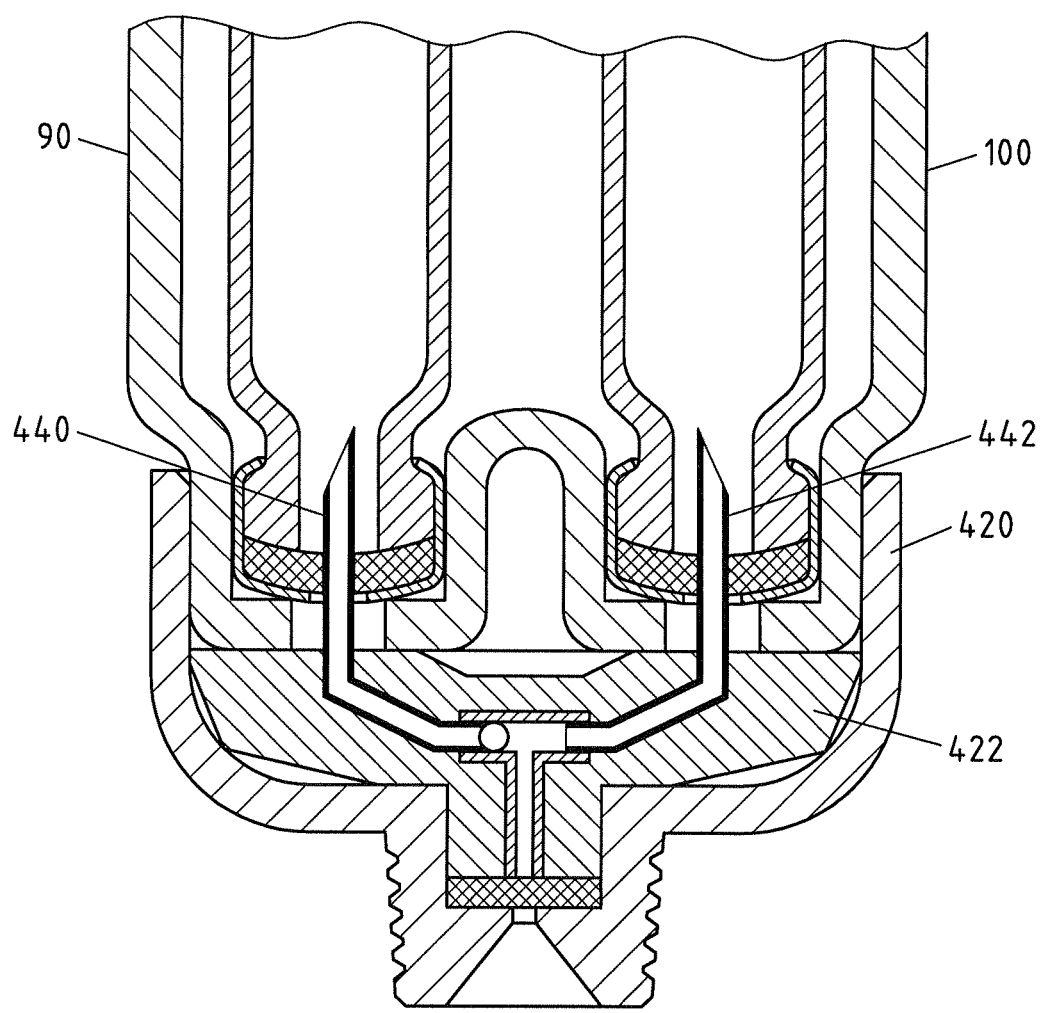
FIG. 20 illustrates a cross-sectional view of the needle hub assembly shown in FIG. 18 mounted in a dispense interface.

FIG. 20 finally shows a cross-sectional view of the needle hub 422 assembly shown in FIG. 18 mounted in a dispense interface 420. The reference numbers used are taken from FIGS. 16 to 19 as well as from FIG. 11, so that the description of these Figures apply here, too. Especially it can be seen from FIG. 20, that the valve and fluid pathway construction including the needles 440 and 442 is connected to reservoirs 90 and 100, which are filled with two different liquid drug components.

Thus a medical device of delivering at least two drug agents from separate reservoirs comprising dispense interface 420, needle hub 422, and the valve and fluid pathway construction according to FIGS. 16 to 19 is described.

Finally and as is shown in FIG. 12, the angle α between the needle 342 and inlet pathway 332 is larger than 100°, especially about 120°. This angle α deviating from a rectangular angle reduces the friction of the flow of liquid through the needle-pathway assembly and results in a better pressure transportation from the cartridge to the central space 308. This again improves the functionality of the valve assembly.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus comprising:
   a valve body comprising a first inlet opening, a second inlet opening, an outlet opening, and a central space connecting the first inlet opening, the second inlet opening, and the outlet opening, and
   a spherical element movably contained inside the central space configured for translatory movement and configured to seal either the first inlet opening or the second inlet opening,
   wherein the first inlet opening and the second inlet opening are configured for fluid communication with a first reservoir and a second reservoir, respectively,
   wherein the outlet opening is configured for fluid connection with a septum.

2. The apparatus of claim 1, wherein the spherical element is configured to be pressed against the first inlet opening, while a pressure of a fluid in the second inlet opening is larger than the pressure of a fluid in the first inlet opening.

3. The apparatus of claim 1, wherein the spherical element comprises a core material and an outer material, wherein the core material is harder than the outer material.

4. A dispense interface configured for fluid communication with a first reservoir and a second reservoir of liquids, especially liquid drug components, comprising,
   a needle hub,
   wherein the needle hub comprises: an apparatus comprising
      a valve body comprising a first inlet opening, a second inlet opening, an outlet opening, and a central space connecting the first inlet opening, the second inlet opening, and the outlet opening; and
      a spherical element movably contained inside the central space configured for translatory movement and configured to seal either the first inlet opening or the second inlet opening,
   wherein the first inlet opening and the second inlet opening are configured for fluid communication with the first reservoir and the second reservoir, respectively, and
   wherein the outlet opening is configured for fluid connection with a septum.

5. The dispense interface of claim 4:
   wherein the first inlet opening is connected via a first inlet pathway with a first needle, the first needle being configured for fluid communication with the first reservoir, and
   wherein the second inlet opening is connected via a second inlet pathway with a second needle, the second needle being configured for fluid communication with the second reservoir.

6. The dispense interface of claim 4, wherein the outlet opening is connected via a holding chamber with a septum.

7. The dispense interface of claim 4, wherein the valve body, the inlet pathways, and the holding chamber are built inside the needle hub.

8. The dispense interface of claim 4, wherein the valve body, the inlet pathways, and the holding chamber are built as separate elements which are configured to be positioned in the needle hub.

9. A medical device configured for delivering at least two drug agents from separate reservoirs, the medical device comprising:
- a dispense interface configured for fluid communication with a first reservoir for a first drug agent and a second reservoir for a second drug agent,
- wherein the dispense interface comprises a needle hub, wherein the needle hub comprises an apparatus comprising:
    - a valve body comprising a first inlet opening, a second inlet opening, an outlet opening, and a central space connecting the first inlet opening, the second inlet opening, and the outlet opening; and
    - a spherical element movably contained inside the central space configured for translatory movement and configured to seal either the first inlet opening or the second inlet opening,
- wherein the first inlet opening and the second inlet opening are configured for fluid communication with the first reservoir and the second reservoir, respectively, and
- wherein the outlet opening is configured for fluid connection with a septum.

\* \* \* \* \*